United States Patent
Tsuboko et al.

(10) Patent No.: US 8,695,588 B2
(45) Date of Patent: Apr. 15, 2014

(54) NEBULIZER

(75) Inventors: Toshi Tsuboko, Isezaki (JP); Eiichi Takano, Tokyo (JP); Satomi Ise, Tokyo (JP)

(73) Assignees: Gunma Koike Co., Ltd., Isezaki-shi (JP); Koike Medical Co., Ltd., Tokyo (JP)

( * ) Notice: Subject to any disclaimer, the term of this patent is extended or adjusted under 35 U.S.C. 154(b) by 318 days.

(21) Appl. No.: 12/991,932

(22) PCT Filed: Mar. 12, 2009

(86) PCT No.: PCT/JP2009/054722
§ 371 (c)(1),
(2), (4) Date: Mar. 3, 2011

(87) PCT Pub. No.: WO2009/139221
PCT Pub. Date: Nov. 19, 2009

(65) Prior Publication Data
US 2011/0168171 A1   Jul. 14, 2011

(30) Foreign Application Priority Data
May 14, 2008   (JP) .................. 2008-126690

(51) Int. Cl.
*A61M 11/00* (2006.01)
*A62B 9/02* (2006.01)

(52) U.S. Cl.
USPC ............. 128/200.21; 128/200.14; 128/205.24

(58) Field of Classification Search
USPC ................... 128/200.14, 200.21, 205.24
See application file for complete search history.

(56) References Cited

U.S. PATENT DOCUMENTS

| 3,836,079 A | | 9/1974 | Huston |
| 4,629,590 A | * | 12/1986 | Bagwell .................. 261/78.2 |
| 4,886,055 A | | 12/1989 | Hoppough |
| 7,143,763 B2 | * | 12/2006 | Abate .................. 128/200.14 |

FOREIGN PATENT DOCUMENTS

| EP | 0473261 A2 | 3/1992 |
| JP | 4-61905 A | 2/1992 |

OTHER PUBLICATIONS

International Search Report issued in corresponding PCT Application No. PCT/JP2009/054722.

* cited by examiner

*Primary Examiner* — Loan Thanh
*Assistant Examiner* — Jennifer M Deichl
(74) *Attorney, Agent, or Firm* — Smith Patent Office

(57) ABSTRACT

A nebulizer capable of supplying oxygen gas of high concentration by increasing the flow rate of the oxygen gas and capable of forming minute aerosol irrespective of a change in the flow rate of the oxygen gas. A nebulizer (A) has a nozzle member (11) for discharging oxygen gas from an orifice (11b), an aerosol forming member (12) mounted at a position corresponding to the orifice, sucking water by suction created by flow of the oxygen gas discharged from the orifice, and forming the sucked water into minute aerosol, and a window (9) and a slit (10) which suck air as the oxygen gas is discharged from the orifice of the nozzle member. The nozzle member (11) has, in addition to the orifice (11b), an oxygen gas outflow section formed in a direction different from that of the orifice and causing supplied oxygen gas to flow thereout according to the pressure of the oxygen gas.

2 Claims, 3 Drawing Sheets ized by aerosol, and also concerns such a nebulizer that
NEBULIZER

TECHNICAL FIELD

The present invention relates to a nebulizer that supplies to a patient a gas having a high oxygen concentration that is humidified by aerosol, and also concerns such a nebulizer that achieves an increase of a flow rate of an oxygen gas and an adjustment of the oxygen gas concentration over a wide range, and also achieves to form fine aerosol regardless of changes in the flow rate of the oxygen gas.

BACKGROUND ART

A nebulizer is used when a gas having a high oxygen concentration is supplied to a patient. The nebulizer is configured by a bottle in which water is contained, and a lid member that is detachably attached to the bottle. The nebulizer is designed so that, by supplying an oxygen gas from a supply unit of the oxygen gas attached to the lid member, water contained in the bottle is sucked, while air is also sucked so that the sucked water is humidified as fine aerosol; thus, gas humidified by the aerosol with a high oxygen concentration can be supplied to a patient.

In the nebulizer, by discharging an oxygen gas from an orifice that is formed on a nozzle member, water contained in the bottle is sucked from a suction pore disposed near the orifice, and by allowing the water to collide with a baffle that is disposed face to face with the orifice, fine aerosol can be formed.

When the aerosol has large particles, they are deposited on an upper respiratory tract of the patient to cause a problem that they are not allowed to reach air vesicles; therefore, it is considered that the size of the particles is preferably set to about 5 μm or less. For this reason, in general, the flow rate of the oxygen gas to be supplied is set in association with the diameter of the orifice. Therefore, a flowmeter is attached to an oxygen piping system to be connected to the nebulizer so that by adjusting the flowmeter, the oxygen flow rate to be supplied to a patient is adjusted. In the case of a nebulizer generally used at present, the flow rate of the oxygen gas is set to 15 liters per minute even in the maximum level.

Near the nozzle member of the nebulizer, a suction pore for air whose opening area is designed to be adjusted is formed, and air having a quantity that corresponds to the degree of opening is sucked from the suction pore according to the discharge of the oxygen gas from the orifice formed in the nozzle member so that a mixed gas of the oxygen gas and aerosol is formed. Therefore, by managing the degree of opening of the suction pore for air and the flow rate of the oxygen gas, an oxygen concentration of a gas to be supplied to a patient can be set, and the quantity of gas supply can also be set.

DISCLOSURE OF INVENTION

Problems to be Solved by the Invention

Depending on the conditions and disease of a patient, a gas having a high oxygen concentration needs to be supplied at a large flow rate. However, as described earlier, in the case of a nebulizer currently used, the quantity of oxygen gas supply is set to 15 liters per minute even in the maximum level, and there is a research report (see Journal of the Japanese Respiratory Society 43(9)2005, 502-507) that shows that, even if an oxygen gas having a flow rate of 15 liters per minute is supplied, the oxygen concentration actually supplied to the patient is 60%.

For this reason, there have been strong demands for a nebulizer that is designed to increase the flow rate of oxygen so as to supply a gas having high concentration. In order to address these demands, when the diameter of an orifice formed in the nozzle member is enlarged, it is possible to increase the flow rate of the oxygen gas.

In this case, however, although no specific problem is raised when the oxygen flow rate is high, the flow velocity of the oxygen gas to be discharged from the orifice is lowered when the oxygen flow rate is lowered, resulting in a problem in that a failure in sucking sufficient water occurs to cause a failure in forming aerosol, that is, a failure in increasing the degree of opening of the suction pore to lower the oxygen concentration.

In other words, in order to address various kinds of patients, it is required to make the adjustment range of the oxygen flow rate wider, and to form desired aerosol over the entire adjustment range so that the oxygen concentration can be adjusted within a wide range. At present, there have been demands for developing a nebulizer that can satisfy these demands.

An object of the present invention is to provide a nebulizer that can increase a flow rate of the oxygen gas and adjust the oxygen gas concentration over a wide range, and also achieves to form fine aerosol independent of a change in the flow rate of the oxygen gas.

Means for Solving the Problems

In order to solve the above-mentioned problems, a nebulizer according to the present invention is provided with: a nozzle member for discharging an oxygen gas from an orifice; an aerosol forming member that is disposed at a position corresponding to the orifice of the nozzle member, and sucks water by the oxygen gas flow discharged from the orifice, while forming the sucked water into fine aerosol; and an air suction pore that sucks air in response to the discharge of the oxygen gas from the orifice of the nozzle member, and in this structure, in addition to the orifice that discharges the oxygen gas toward the aerosol forming member, the nozzle member has an oxygen gas flow-out unit that has a circulation pore for an oxygen gas, formed in a direction different from the orifice, and allows the oxygen gas to flow from the circulation pore for the oxygen gas in response to a pressure of the oxygen gas supplied thereto so that the oxygen gas is discharged from the orifice in response to the pressure of the supplied oxygen gas, or the oxygen gas is discharged from the orifice, while being also allowed to flow out from the oxygen gas flow-out unit.

In the above-mentioned nebulizer, the nozzle member is provided with: an orifice that discharges an oxygen gas toward the aerosol forming member along an axial core of the nozzle member; a flow-out pore that is formed on a side wall of the nozzle member so as to form an oxygen gas flow-out unit, and a valve, disposed on a peripheral portion of the nozzle member at a position opposed to the flow-out pore, that closes the flow-out pore in a state where no oxygen gas is supplied to the nozzle member, and opens the flow-out pore in response to the pressure of the oxygen gas supplied to the nozzle member.

Effect of the Invention

In the nebulizer according to the present invention, an oxygen gas flow-out unit which, in response to a pressure of an oxygen gas supplied thereto, allows the oxygen gas to flow out, is formed in the nozzle member, in addition to the orifice; therefore, in the case where the pressure of the supplied oxygen gas is lower than a predetermined pressure, the oxygen gas is discharged only from the orifice. By maintaining the diameter of the orifice, the diameter of the water suction pore in the aerosol forming member, the shape of the baffle and the like so as to have such a relationship as to form fine aerosol (for example, the relationship of a nebulizer that is currently utilized), a mixed gas of water and an oxygen gas is allowed to collide with the baffle so that fine aerosol can be formed.

When the pressure of the oxygen gas supplied to the nozzle member increases to exceed a predetermined value, the oxygen gas is allowed to flow out also from the flow-out pore so that the flow rate of the oxygen gas is increased. At this time, since there is no big change in the flow rate and flow velocity of the oxygen gas to be discharged from the orifice, a forming state of fine aerosol can be maintained.

Since a valve that closes the flow-out pore in a state where no oxygen gas is supplied to the nozzle member, and opens the flow-out pore in response to the pressure of the oxygen gas supplied to the nozzle member is disposed on a peripheral portion of the nozzle member at a position opposed to the flow-out pore, the flow-out pore is opened when the oxygen gas supplied to the nozzle member becomes higher than a pressure by which the valve is activated, the flow-out pore is opened so that the supplied oxygen gas can be supplied through the orifice and the flow-out pore.

EXPLANATION OF REFERENCE NUMERALS

Figure 1:
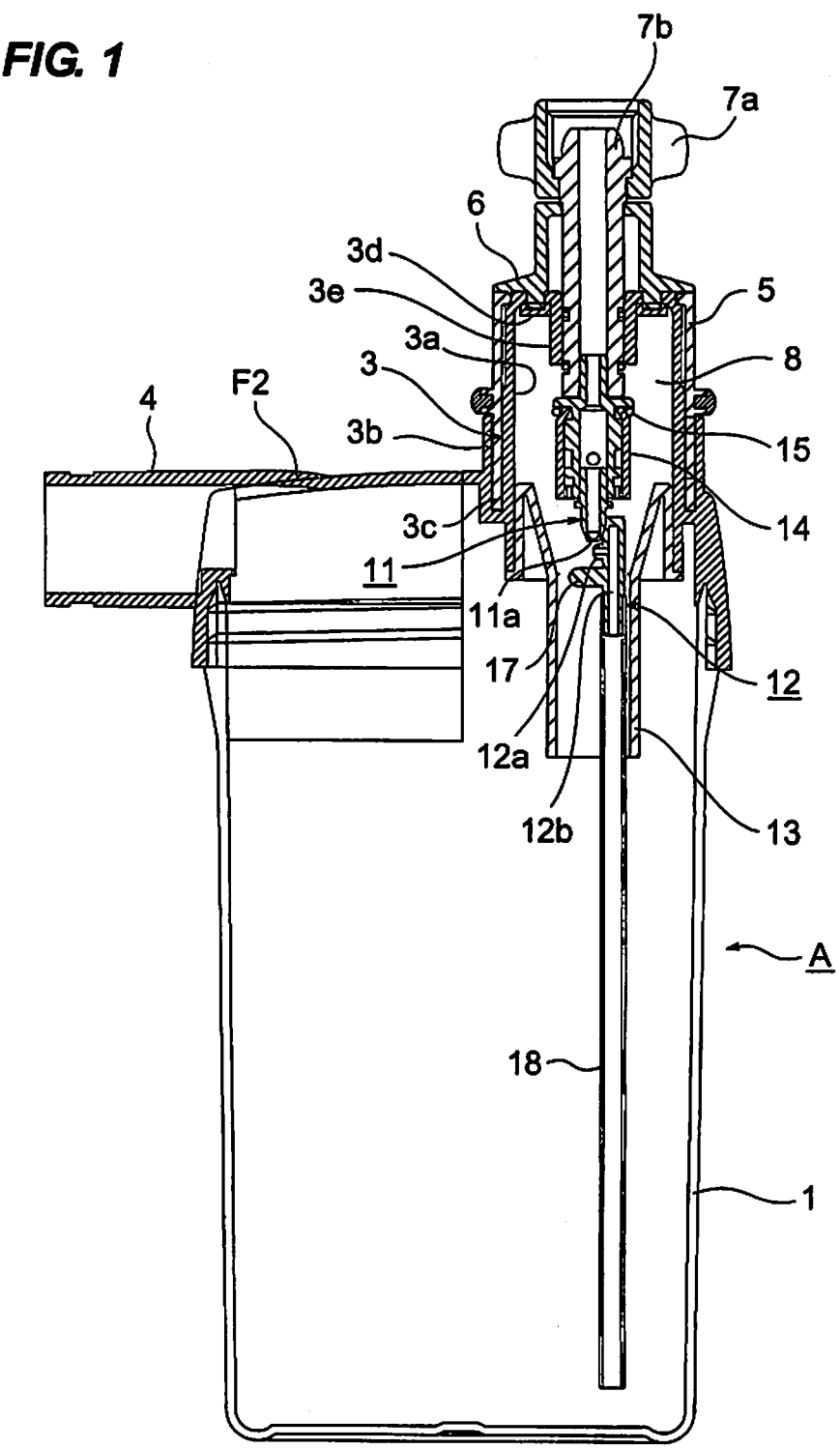
FIG. 1 is a cross-sectional view that explains a structure of a nebulizer.

A nebulizer
1 bottle
2 cap
3 upright protrusion
3*a*, 3*b* protrusion
3*c* groove
3*d* top board
3*e* sleeve
4 horizontal protrusion
5 adjustment dial
5*a* mark
6 indication member
6*a* indication unit
7*a* cap nut
7*b* terminal
8 enclosed space
9 window
10 slit
11 nozzle member
11*a* circulation pore
11*b* orifice
11*c* flow-out pore
11*d*, 11*e* groove
11*f*, 11*g* flange
11*h* pore
12 aerosol forming member
12*a* suction pore
12*b* passage
13 diffuser
14 tube
15 O-ring
17 baffle
18 tube

BEST MODE FOR CARRYING OUT THE INVENTION

Figure 2:
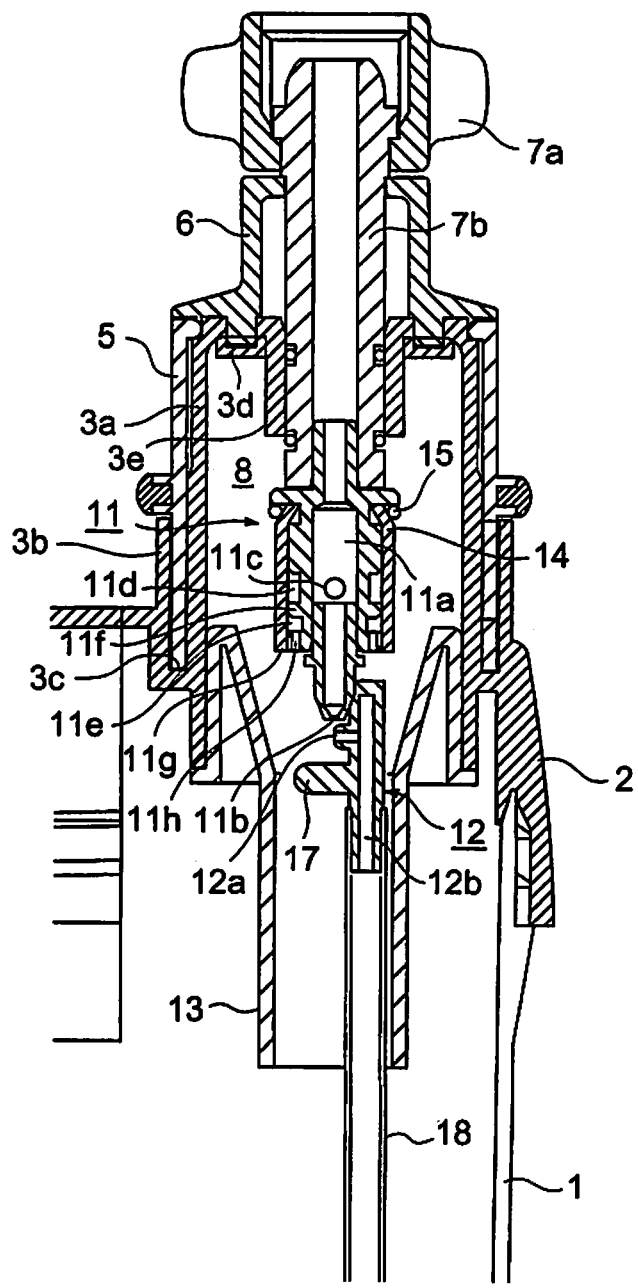
FIG. 2 is an enlarged view that explains a structure of a peripheral portion of a nozzle member.
Figure 3:
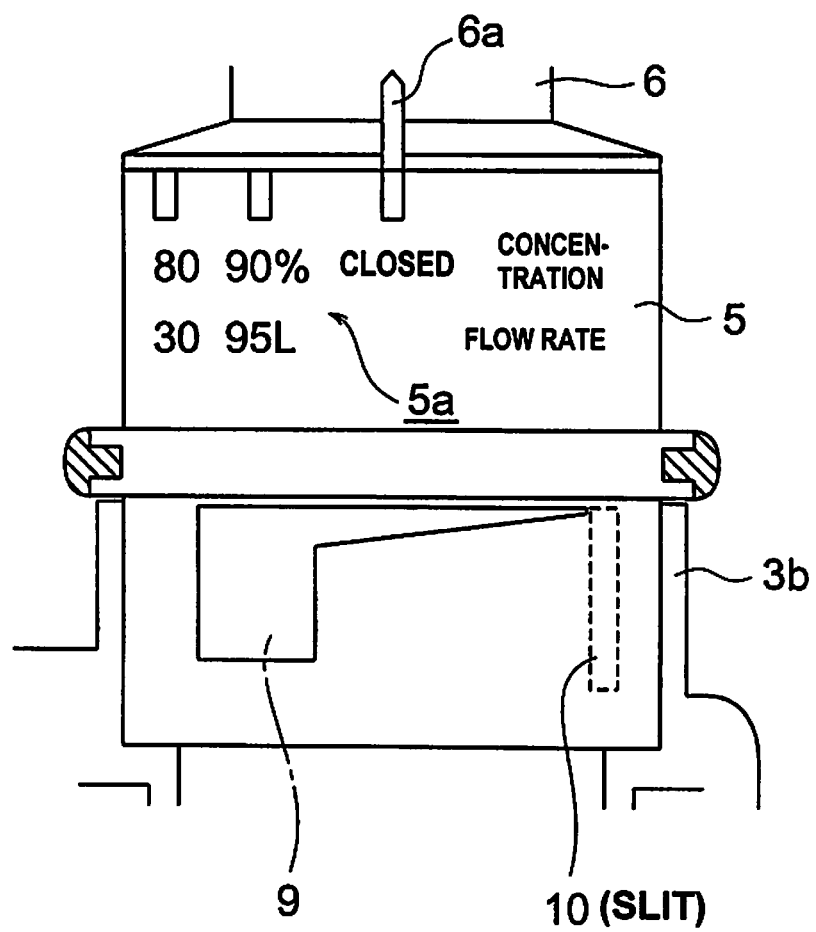
FIG. 3 is an explanatory drawing that explains a dial used for adjusting an oxygen concentration of a gas to be supplied to a patient.

Referring to drawings, the following description will discuss a structure of a nebulizer. FIG. 1 is a cross-sectional view that shows the structure of the nebulizer. FIG. 2 is an enlarged drawing that explains the structure of a peripheral portion of a nozzle member. FIG. 3 is an explanatory drawing that explains a dial used for adjusting an oxygen concentration of a gas to be supplied to a patient.

A nebulizer A, shown in the drawings, is designed so as to supply to a patient a gas that has a high oxygen concentration and is humidified by fine aerosol. This nebulizer A includes a bottle 1 in which water is contained, a supply system for an oxygen gas, and a cap 2 in which a system for feeding a moistened gas with a high oxygen concentration to a patient is assembled. The cap 2 is detachably attached to the upper end of the bottle 1 by means of screw coupling.

A cylindrical upright protrusion 3 is formed on the cap 2 in a direction (vertical direction) corresponding to a longitudinal direction relative to the nebulizer A placed upright, and an oxygen gas supply system is formed in the upright protrusion 3. Moreover, on the side apart from the upright protrusion 3 of the cap 2, a cylindrical horizontal protrusion 4 is formed in a direction (horizontal direction) corresponding to a lateral direction relative to the nebulizer A placed upright, and an arrangement is made so as to send and supply a mixed gas of air, oxygen gas and aerosol to a patient from this horizontal protrusion 4.

The upright protrusion 3 is composed of two cylindrical protrusions, and between an inner protrusion 3*a* and an outer protrusion 3*b*, a groove 3*c* is formed so that an adjustment dial 5 is fitted thereto so as to pivot thereon. Moreover, the top portion of the inner protrusion 3*a* is tightly sealed by a top board 3*d*. Thus, an enclosed space 8, formed by the protrusion 3*a* and the top board 3*d*, is placed inside the inner protrusion 3*a* forming the upright protrusion 3.

In the center of the top board 3*d*, a sleeve 3*e* is formed, and an indication member 6, which indicates the pivotal position of the adjustment dial 5, is secured onto the top board 3*d*. Moreover, a terminal 7*b* to which a cap nut 7*a* is attached is fitted to the sleeve 3*d*, and the cap nut 7*a* is connected to the outlet of an oxygen flow meter, not shown, so that oxygen gas is supplied.

As shown in FIG. 3, a window 9 is formed on the side face of the adjustment dial 5. This window 9 has one side (left side of the window 9) having a virtually rectangle shape and is designed to form a virtually triangular shape from the rectangle shape toward the other side (right side of the window 9). That is, the window 9 is formed so as to have its area changed from the one side toward the other side. Moreover, a slit 10 having a predetermined width is formed on the side face of the inner protrusion 3*a* at a position opposed to the window 9. Thus, an opening, formed by the window 9 and the slit 10, functions as an air suction pore.

Therefore, by allowing the adjustment dial 5 to pivot so that the window 9 is made face to face with the slit 10, an opening that has an area composed of the longitudinal dimension of the window 9 and the width dimension of the slit 10, and communicates with the enclosed space 8 is formed. That is, by adjusting the pivotal position of the adjustment dial 5, the opening area relative to the enclosed space 8 is adjusted so that the introduction quantity of air can be adjusted.

Moreover, an indication unit 6a is formed on the indication member 6, and a mark 5a that indicates the flow rate and concentration of the oxygen gas is displayed on the outside surface of the adjustment dial 5. That is, by allowing the adjustment dial 5 to pivot so that the mark 5a is made coincident with the indication unit 6a, with the flow rate of the oxygen gas being adjusted to the value indicated by the mark 5a, the oxygen concentration indicated by the mark 5a is available.

A nozzle member 11 is fitted to the end portion of the terminal 7b on the bottle 1 side. Moreover, an aerosol forming member 12 is placed near the nozzle member 11. Since the nozzle member 11 and the aerosol forming member 12 have different functions, these members may be prepared as two different members, and these two members may be combined with each other to form the corresponding structure.

In this case, however, since the positional relationship between the oxygen gas flow discharged from the nozzle and the suction pore for sucking water, as well as the positional relationship between the orifice and the baffle, the nozzle member 11 and the aerosol forming member 12 are preferably formed into one integral unit. In the present embodiment, the nozzle member 11 and the aerosol forming member 12 are integrally designed as one member.

One end of the protrusion 3a formed on the cap 2 is extended toward the inner side of the cap 2, and a nozzle-shaped diffuser 13 is disposed on this extended portion. The diffuser 13 is formed into not a delta shape, but a tapered shape with its upper tip portion being narrowed, and a portion below the taper-shaped portion is formed into a straight tube shape. Moreover, the nozzle member 11 is disposed at the taper-shaped portion of the diffuser 13.

In the nozzle member 11 and the diffuser 13, thus disposed, since an oxygen gas, discharged from the nozzle member 11, is allowed to pass through the diffuser 13 at a high speed, air located in the enclosed space 8 is sucked, and allowed to flow toward the diffuser 13 side. At this time, air is sucked according to the area of the opening, composed of the window 9 and the slit 10, that has been formed in association with the pivotal position of the adjustment dial 5, and allowed to pass through the diffuser 13.

In the nozzle member 11, a circulation pore 11a through which oxygen gas is allowed to flow is formed in its center, and an orifice 11b that communicates with the circulation pore 11a is also formed at its tip, with a flow-out pore 11c being formed on its side face. Moreover, on the outside surface of the nozzle member 11, grooves 11d and 11e, each having a ring shape, are formed at a position corresponding to the flow-out pore 11c as well as at a tip side position, and flanges 11f and 11g are formed between these grooves 11d and 11e, as well as at a tip side position of the groove 11e. A plurality of pores through which oxygen gas is allowed to flow is formed on the flange 11g.

A tube 14, which forms a valve, is fitted to the peripheral surface of the nozzle member 1. The tube 14 is made from a material that has appropriate elasticity and flexibility, and designed so that its inner diameter is made virtually equal to the outer diameter of each of the flanges 11f and 11g of the nozzle member 11. An O-ring 15 is attached to the upper tip side of the tube 14 fitted to the nozzle member 11, and with the O-ring 15 being attached thereto, a flow-out toward the upper portion and vibrations of the tube are prevented.

The above-mentioned flow-out pore 11c, grooves 11d, 11e, flanges 11f, 11g and tube 14 are allowed to form an oxygen gas flow-out unit.

The tube 14, which forms a valve as described above, has such functions that, in a state where no oxygen gas is supplied to the circulation pore 11a of the nozzle member 11, the flow-out pore 11c is closed, and that in response to the pressure of an oxygen gas supplied to the circulation pore 11a, the flow-out pore 11c is opened.

In this manner, in the present embodiment, not a structure in which the tube 14 directly closes the flow-out pore 11c, but a structure in which the groove 11d to be used for opening the flow-out pore 11c can be closed is prepared. That is, in the present invention, even such a structure as not to directly open and close the flow-out pore 11c is designed to serve as a valve, as long as it can substantially carry out opening and closing operations of the flow-out pore 11.

The pressure to be used upon opening the flow-out pore 11c formed in the nozzle member 11 is not particularly limited, and in the case where the quantity of an oxygen gas to be supplied to a patient is greater than the critical flow rate of the oxygen gas to be discharged from the orifice 11b, the flow-out pore 11c is preferably opened so as to allow the portion exceeding the critical flow rate to flow out.

In particular, in the case of an oxygen pipe system in a hospital, the pressure of the oxygen gas to be supplied to the oxygen pipes is legally regulated (about 0.39 MPa (4 Kg/cm$^2$)); therefore, the flow rate of the oxygen gas and the pressure of the oxygen gas in the circulation pore 11a of the nozzle member 11 are correlated with each other. Therefore, by using a tube 14 having appropriate elasticity (spring constant) and flexibility, the tube 14 is deformed so that the flow-out pore 11c is opened, when the pressure of the oxygen gas at the circulation pore 11a of the nozzle 11 exceeds a predetermined pressure.

In the present embodiment, the flow-out pore is designed so as to release oxygen at a flow rate in a range from 12 liters per minute to 15 liters per minute. The pressure inside the circulation pore 11a of the nozzle member 11 to which oxygen at that flow rate is supplied is set to about 0.11 MPa to 0.13 MPa. For this reason, as the tube 14, a tube made from silicone rubber that is designed to be deformed at the above-mentioned pressure is used.

Moreover, as the structure of the valve, the tube 14 of the present embodiment is not necessarily required to be used, and a valve member capable of being opened and closed may be placed outside the flow-out pore 11c so that this valve member can be pressed toward the flow-out pore 11c side by an elastic member such as a spring, and rubber so as to provide the corresponding structure. In this case, by setting the spring constant of the spring or rubber on demand, a pressure required for opening the flow-out pore 11c can be set.

The aerosol forming member 12 has a structure in which a water suction pore 12a is formed near the orifice 11a of the nozzle member 11, and a passage 12b used for sucking water is continuously formed along the suction pore 12a. Moreover, a baffle 17 is formed at a position separated from the suction pore 12a. This baffle 17 is formed at such a position opposed to the orifice 11a of the nozzle member 11 that the sucked water is allowed to collide therewith in a state with a sufficient speed so that fine aerosol can be formed.

A tube 18 is fitted to a lower portion of the aerosol forming member 12 so as to be connected to the passage 12b. This tube 18 is disposed at such a position that its end portion is brought close to the bottom surface of the bottle 1 so that water contained in the bottle 1 can be sucked efficiently.

The following description will discuss the function of the nebulizer A having the above-mentioned structure. A predetermined amount of water is contained in the bottle 1, and a cap nut 7a is connected to an oxygen flow meter, not shown, with the horizontal protrusion 4 being connected with a tube to which an oxygen mask, not shown, is attached.

The adjustment dial 5 is rotated in response to an oxygen concentration to be supplied to a patient so that a mark 5a (for example, 90% in concentration and 35 L in flow rate) corresponding to a designated concentration is made face to face with the indication unit 6a of the indication member 6. By this rotation of the adjustment dial 5, the window 9 formed on the pivotal adjustment dial 5 is made face to face with the slit 10 so that an opening having an area composed of the dimension of the window 9 in a longitudinal direction and the width direction of the slit 10 is formed.

Next, by operating the oxygen flow meter, the flow rate is set to 35 L. By this adjustment, an oxygen gas of 35 liters per minute is supplied to the nozzle member 11. The oxygen gas thus supplied has its one portion discharged from the orifice 11b through the circulation pore 11a, while water is sucked from the suction pore 12a formed in the aerosol forming member 12, and mixed into the oxygen gas. Moreover, the mixed gas of the oxygen gas and water is allowed to collide with the baffle 17 so that fine aerosol is formed, and a mixed gas of the oxygen gas and the aerosol is allowed to pass through the diffuser 13.

Moreover, since the inner pressure of the circulation pore 11a to which the oxygen gas at 35 liters per minute has been supplied is higher than the aforementioned rate of 0.13 MPa, the pressure is exerted on the tube 14 plugging the groove 11d, and the tube 14 is subsequently deformed to be expanded. The deformation of the tube 14 forms a gap between the flange 11f and the tube 14 so that the oxygen gas is allowed to flow toward the groove 11e side through the gap. Then, the oxygen gas flowing through the groove 11e is allowed to pass through the pore 11h to flow toward the diffuser 13 side.

That is, the oxygen gas simultaneously flows toward the diffuser 13 side through the orifice 11b serving as the nozzle member 11 and the flow-out pore 11c so that the flow rate can be increased. Moreover, as the oxygen gas increased in flow rate as described above and aerosol pass through the diffuser 13, air is allowed to flow to the inside of the enclosed space 8 from the opening composed of the window 9 and the slit 10. The flow-in air is allowed to flow toward the diffuser 13 side to form a mixed gas of the oxygen gas and aerosol so that the resultant gas is supplied to a mask of a patient through the horizontal protrusion 4.

In this manner, the gas having a high oxygen concentration can be supplied to the patient with a desired humidified state being maintained.

Moreover, in the case where a gas having a low oxygen concentration with a lowered oxygen flow rate (12 liters per minute or less) is supplied to a patient, that is, for example, in the case of an oxygen flow rate of about 10 liters per minute, the adjustment dial 5 is rotated to make the mark corresponding to a flow rate of 10 L face to face with the indication unit 6a of the indication member 6, with the oxygen flow meter being operated, so that the oxygen flow rate is adjusted to 10 liters per minute.

Thus, the oxygen gas whose flow rate is adjusted to 10 liters per minute is supplied to the circulation pore 11a of the nozzle member 11, and the inner pressure of the circulation pore 11a is subsequently lowered to a pressure of about 0.11 MPa or less. This pressure is exerted on the tube 14 from the circulation pore 11c through the groove 11d. When subjected to the pressure, the tube 14 is deformed according to the pressure exerted thereon; however, such a deformation as to form the gap relative to the flange 11f is not made so that the oxygen gas is discharged only from the orifice 11b.

The oxygen gas, discharged from the orifice 11b of the nozzle member 11 is ensured in its sufficient flow rate, and water is sucked from the suction pore 12a of the aerosol forming member 12, and allowed to collide with the baffle 17 so that desired aerosol can be formed.

In this manner, since the flow rate of the oxygen gas discharged from the orifice is maintained in a sufficiently high level, it is possible to form desired aerosol even in the case of a low flow rate of the oxygen gas. That is, although the adjustment range of the oxygen gas flow rate is expanded, it is possible to stably form aerosol, and consequently to supply a desired gas in a preferably humidified state to a patient.

INDUSTRIAL APPLICABILITY

The nebulizer of the present invention makes it possible to sufficiently expand the range of an oxygen gas flow rate in comparison with the conventional nebulizer, and consequently to form desired aerosol over the expanded range. For this reason, the nebulizer can be applied to a large number of patients having different symptoms.

The invention claimed is:

1. A nebulizer comprising:
a nozzle member for discharging an oxygen gas from an orifice;
an aerosol forming member that is disposed at a position corresponding to the orifice of the nozzle member, including a suction pore for sucking water by the oxygen gas flow discharged from the orifice and a baffle for forming the sucked water into a fine aerosol;
an air suction pore that sucks air in response to the discharge of the oxygen gas from the orifice of the nozzle member;
wherein the nozzle member includes the orifice that discharges the oxygen gas toward the aerosol forming member along an axial core of the nozzle member;
a flow-out pore of the oxygen gas is formed on a side wall of the nozzle member,
a valve that is disposed on a peripheral portion of the nozzle member at a position opposed to the flow-out pore closes the flow-out pore in a state where no oxygen gas is supplied to the nozzle member and opens the flow-out pore in response to a pressure of the oxygen gas supplied to the nozzle member; and
when the pressure of the oxygen gas supplied thereto is less than a predetermined value, the oxygen gas is discharged from the orifice, and when the pressure of the oxygen gas supplied thereto is higher than the predetermined value, the oxygen gas is discharged from the orifice, while being also allowed to flow out from the flow-out pore to be mixed with the aerosol.

2. The nebulizer according to claim 1, wherein on an outside surface of the nozzle member, a first groove having a ring shape is formed at a position corresponding to the flow-out pore, and a second groove is formed at an orifice side of the first groove with a first flange interposed between the first groove and the second groove;
a pore through which the oxygen gas is allowed to flow from the second groove is formed on a second flange that is formed at a tip side position of the nozzle member;
the valve is formed of a tube that has elasticity and flexibility and has an inner diameter substantially equal to an outer diameter of the nozzle member; and the tube is fitted to the peripheral portion of the nozzle member, one end of the tube is fixed to the side wall, and the other end of the tube extends to the second flange.

* * * * *